United States Patent [19]
Yonkers et al.

[11] 3,972,222
[45] Aug. 3, 1976

[54] METHOD AND APPARATUS FOR TESTING ARTICLES EMPLOYING A SMALL ARMS PRIMER
[75] Inventors: Edward H. Yonkers; Floyd B. Nagle, both of Midland, Mich.
[73] Assignee: The Dow Chemical Company, Midland, Mich.
[22] Filed: Sept. 1, 1972
[21] Appl. No.: 285,575

[52] U.S. Cl. .................................................. 73/12
[51] Int. Cl.² ........................................ G01N 3/30
[58] Field of Search .................. 73/12, 49.4, 102

[56] References Cited
UNITED STATES PATENTS

| 2,197,585 | 4/1940 | Lundquist | 73/12 |
| 2,868,128 | 1/1959 | Ramsey | 102/86.5 |
| 2,966,791 | 1/1961 | Ivins | 73/12 |
| 3,085,422 | 4/1963 | Monroe | 73/12 |
| 3,248,924 | 5/1966 | Boynton | 73/12 |
| 3,260,103 | 7/1966 | Johnson | 73/12 |

Primary Examiner—Herbert Goldstein
Attorney, Agent, or Firm—Robert B. Ingraham

[57] ABSTRACT

A small detonating device such as a rifle, pistol or shotgun primer or percussion cap is employed to provide gas and/or hydraulic pressure for the testing of the relative strength of articles such as plastic containers, sheet, tube and the like.

1 Claim, 2 Drawing Figures

METHOD AND APPARATUS FOR TESTING ARTICLES EMPLOYING A SMALL ARMS PRIMER

In the preparation of plastic articles it is often desirable to have at least a relative indication of the strength of such articles and their resistance to impact. Containers, such as small screw top bottles, are extremely difficult to evaluate in a rapid manner. Similarly, flat material such as sheet stock can also require considerable time and effort in order to obtain a meaningful evaluation of its impact resistance. Oftentimes in the preparation of containers it is desirable to alter the fabricating conditions to obtain articles of the highest physical properties obtainable with a particular batch of feed stock.

In order to optimize operating conditions it is desirable that there be available a relative test which can be rapidly performed which would evaluate the product being prepared.

It would also be desirable if there were available an improved method for the testing of plastic products.

It would further be desirable if such a method were rapid and inexpensive.

These features and other advantages in accordance with the present invention are achieved in a method for the tesing of plastic articles wherein a plurality of test pieces are subjected to rapidly applied force until permanent deformation of the article occurs, the improvement which comprises applying the force by means of gas generated by a detonating composition.

Also contemplated within the scope of the present invention is a testing apparatus, the testing apparatus comprising a sample support means, the sample support means having sample engaging means adapted to generally circumferentially engage at least a portion of a work piece to be tested, means defining a chamber and a gas passage, the gas passage communicating with a region encompassed by the peripheral engaging means and a detonator activating means in operative combination with said chamber and adapted to activate a detonating device placed therein.

Further features and advantages of the present invention will become more apparent from the following specification taken in connection with the drawing wherein.

Figure 1:
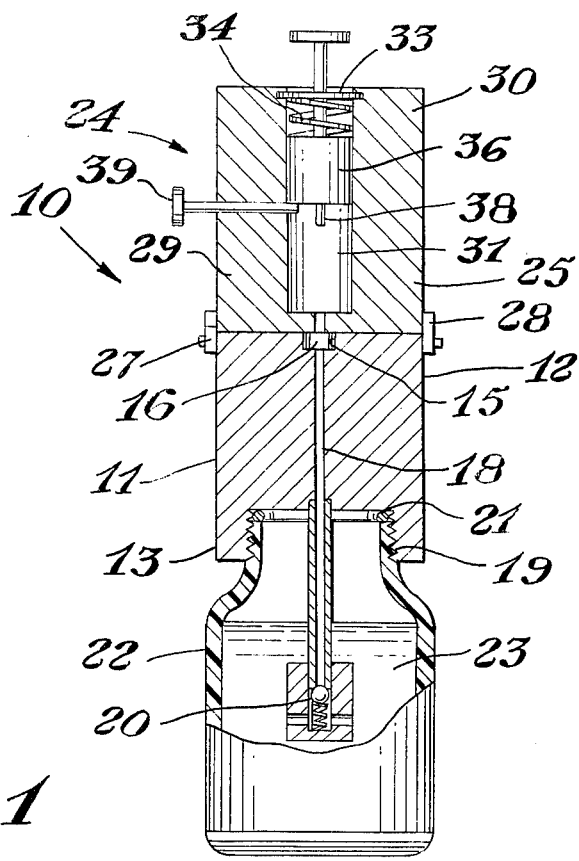
FIG. 1 depicts a schematic cutaway view of an apparatus in accordance with the present invention.

In FIG. 1 there is schematically depicted an apparatus in accordance with the present invention generally designated by the reference numeral 10. The apparatus 10 comprises a body or housing 11. The body 11 has a first end 12 and a second end 13. The first end 12 defines a chamber 15 having disposed therein a detonating device or primer 16. The body 11 defines a passageway 18 extending from the chamber to the second end 13. The passageway 18 terminates in a spring loaded ball check valve 20. The check valve 20 is advantageously removeable and provides a means to dampen the gas pulse generated by the primer. The second end 13 defines a work piece engaging means 19. The means 19 is an internally threaded circular cavity having disposed therein a gas sealing means or O-ring 21. A container 22 is in sealing engagement with the cavity 19 and the O-ring 21. A liquid 23 is disposed within the container 22. Adjacent the second end 13 of the body 11 is an activating means 24. The activating means 24 comprises a body 25 releaseably affixed to the body 11 by connecting means 27 and 28 which beneficially are bayonet-type connectors. The housing 25 has a first end 29 and a second end 30. A cavity 31 extends from the first end to the second end. The cavity 31 has a sharply reduced diameter adjacent the first end 29 and is in full communication with the chamber 15. Adjacent the second end 30 of the body 25 is a retaining means such as a snap ring 33. In operative engagement with a helical compression spring 34 remote from the retaining means 33 is a firing striker 36 resiliently tensioned toward the second end 29 of the body 25. The striker 36 has a firing pin or detonator activator 38 adapted to project from the body 25 and enter the chamber 12. A release or trigger 39 is slidably disposed in the body 25 and prevents movement of the striker 36 toward the chamber 15.

In operation of the device as depicted in FIG. 1, a container to be tested is placed within the cavity 19 and maintained in sealing engagement with sealing means 21. A primer is placed in the chamber 15. The activating means 24 is attached to the body 11 after the striker is positioned generally adjacent the second end 30 of the body 25 and is securely retained by the trigger 39. The entire assembly is placed within a container such as a trash can or the like, the trigger moved outwardly to permit the firing pin to rapidly contact the detonator. The detonating means conveniently is a Boxer or Berdan-type small arms primer. The apparatus 10 is readily decapped by removing the spent primer by using a decapping tool for Berdan primers. If the container has not ruptured, water or other liquid is added thereto and the test repeated until a volume of water is obtained which results in rupture of a portion of the containers so tested. If, in evaluating containers using the previously determined volume of water therein, the fraction of containers which rupture increases, the strength of the containers is decreasing, whereas when rupture is not obtained the strength of the containers is increasing.

Figure 2:
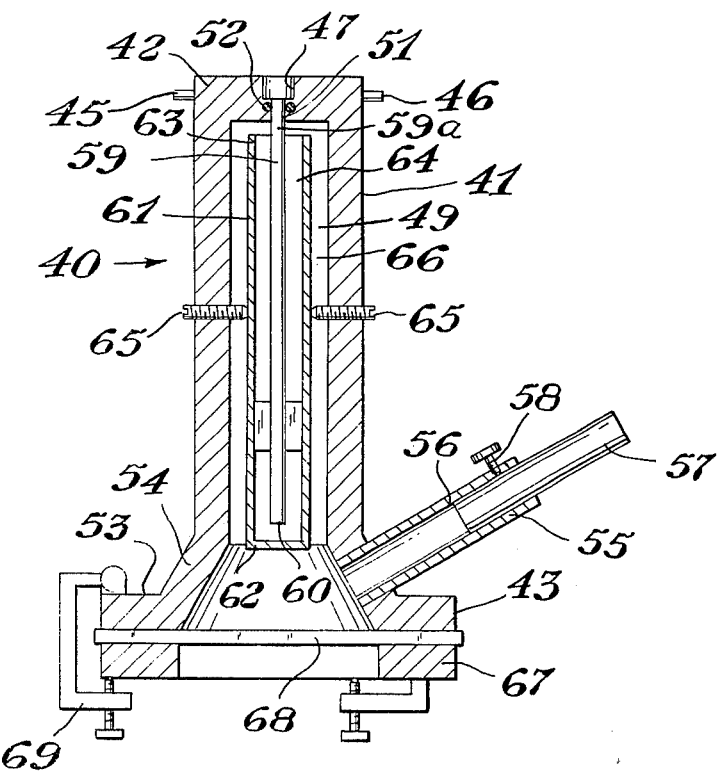
FIG. 2 is a schematic cutaway view of a modified apparatus in accordance with the invention.

In FIG. 2 there is depicted an alternate embodiment of the invention generally designated by the reference numeral 40. The embodiment 40 is particularly adapted for the evaluation of flat or sheet samples. For convenience of illustration, no detonating activator is shown. The device 40 comprises a body portion 41 having a first end 42 and a second end 43. The first end 42 has bayonets or locking pins 45 and 46 adapted to fire a firing mechanism such as the actuator 38 of FIG. 1. The second end 42 defines a detonator receiving chamber or primer pocket 47. The body 41 defines an internal cavity 49 extending generally from the first end 42 to the second end 43. The cavity 49 is in communication with the chamber 47 by means of a narrowed portion 51 having disposed therein a gas sealing means 52 such as an O-ring. At the second end 43 of the body 41 there is defined a generally radially extending flange 53. An outwardly flaring portion 54 is adjacent the flange 53 and a corresponding enlarged portion of the cavity 49. A volume varying means 55 is affixed to the body 41 adjacent the second end 43. The volume varying means comprises a hollow cylindrical body 56 in communication with the cavity 49. The body 56 has disposed therein a piston 57 and is adjustably positioned within the cylinder 56 by locking means 58 such as a set screw. A first or inner conduit 59 is disposed within the cavity 49. The conduit 59 has a first end 59a and a second end 60. The first end 59a and the conduit 59 are in sealing engagement with the gas sealing means 52. The conduit 59 is rigidly affixed to a second conduit 61. The conduit 61 has a closed end 62 and an open end 63. The closed end 62 is positioned generally adjacent the closed end 42 and the body 56. An annular space 64 is defined between the conduits 59 and 61. The conduit 61 and the body 41 define an outer annular space 66. The conduit 61 is maintained in position by retaining screws 65. Adjacent the second end 43 of the body 40 is a clamping ring 67 and a specimen 68. The specimen 68 is disposed between the clamp ring 58 and the specimen maintained in position by a plurality of clamps 69, only two shown.

In operation of the apparatus of FIG. 2, a specimen such as the specimen 68 is clamped in position by means of the ring 67 and the flange 53. A detonating device is placed in the chamber 47, the detonating device activated, gas passes through the conduit 59 and annular space 66, discharging the gas at the second end 60 of the tube 59, the gas passing upwardly within the annular space 64 between the tubes 59 and 61, discharges from the second end of the tube 63 to the tube 61 and passes through the outer annular space 66 and applies gas pressure to the specimen 68. If the specimens 68 rupture, the piston 57 is moved outwardly; that is, in a direction which will increase the volume of the gas within the apparatus until a predetermined percentage of the samples rupture, for example, 50 percent. Repeated testing of the product readily determines whether the specimens become stronger or weaker. Beneficially, the apparatus of FIG. 2 provides a lower loading rate for the specimen due to the baffle of the gas discharged from the detonating device and permits cooler gas than if direct discharge of the gas onto the sample is employed. If desired, the screws 65 may be eliminated and the tube 59 may be maintained in position with interrupted threads and by a ¼ turn rotation of the tube 61 it can be released from the body 40. By forcing the tube 61 into the chamber 47, the spent primer can be removed.

A wide variety of detonating devices are useable in the apparatus and method of the present invention. Particularly advantageous are primers commonly used in small arms such as Boxer and Berdan primers for large and small pistol and large and small rifle as well as shotgun shell primer. Percussion caps widely distributed for use with caplock black powder arms are also readily employed. Percussion caps offer a distinct advantage in the ease with which they can be removed from the supporting nipple after being fired. In repeated service they do not appear to provide as desirable a gas seal or the uniformity as is obtained employing Boxer or Berdan primers.

By way of further illustration, a variety of plastic containers and plastic sheets are evaluated for impact resistance employing apparatus generally as depicted in FIGS. 1 and 2 with and without a check valve, with and without an auxiliary air chamber such as provided by enlarging the passageway 18 of FIG. 1 using rifle primers, pistol primers and shotgun primers. In some instances a Kestler Model 606A pressure transducer connected to an oscilloscope is employed to provide an indication of peak pressures. By varying the internal gas space peak pressures suitable for testing of thin plastic film such as about 10 pounds per square inch up to about 1000 pounds per square inch are obtained. In the testing of plastic sheets, the sheets can be subjected to sufficient pressure to cause them to rupture, or alternately, reduced pressures are employed to provide a sheet which has been bulged. Measurement of the height or depth of the bulge is indicative of the resistance to deformation of the material. In a generally similar manner, a wide variety of plastic shaped articles are readily evaluated for resistance to deformation; e.g., pipe, tubing, pipe and tubing fittings and the like.

The principle of the present invention is readily applied to the testing of a wide variety of plastic materials and has been successfully used with materials varying from polytetrafluoroethylene to impact polystyrene and unmodified polystyrene.

As is apparent from the foregoing specification, the present invention is susceptible of being embodied with various alterations and modifications which may differ particularly from those that have been described in the preceding specification and description. For this reason, it is to be fully understood that all of the foregoing is intended to be merely illustrative and is not to be construed or interpreted as being restrictive or otherwise limiting of the present invention, excepting as it is set forth and defined in the hereto-appended claims.

What is claimed is:

1. A testing apparatus, the testing apparatus comprising
   a sample support means, the sample support means having
   a sample engaging means adapted to generally circumferentially engage at least a portion of the work piece to be tested and wherein said sample engaging means is generally planar and adapted to engage a flat sheet,
   means defining a chamber, a portion of said chamber being sized to receive in generally gas sealing engagement a small arms primer,
   a gas passage, the gas passage communicating with the region encompassed by the peripheral engaging means, and
   a primer activating means in operative combination with said chamber and adapted to activate a primer placed therein.

* * * * *